(12) United States Patent
Riemenschneider

(10) Patent No.: US 11,090,420 B2
(45) Date of Patent: Aug. 17, 2021

(54) DEVICE FOR EXTRACORPOREAL BLOOD TREATMENT INVOLVING A CHANGE OF CONCENTRATE

(71) Applicant: B. BRAUN AVITUM AG, Melsungen (DE)

(72) Inventor: Heiko Riemenschneider, Wagenfurth (DE)

(73) Assignee: B. BRAUN AVITUM AG, Melsungen (DE)

( * ) Notice: Subject to any disclaimer, the term of this patent is extended or adjusted under 35 U.S.C. 154(b) by 0 days.

(21) Appl. No.: 16/407,419

(22) Filed: May 9, 2019

(65) Prior Publication Data
US 2019/0262521 A1 Aug. 29, 2019

Related U.S. Application Data

(63) Continuation of application No. 15/495,449, filed on Apr. 24, 2017, now abandoned.

(30) Foreign Application Priority Data

Apr. 25, 2016 (DE) ...................... 10 2016 107 589.2

(51) Int. Cl.
*A61M 1/00* (2006.01)
*A61M 1/16* (2006.01)
(52) U.S. Cl.
CPC ........ *A61M 1/1656* (2013.01); *A61M 1/1601* (2014.02); *A61M 1/1607* (2014.02);
(Continued)

(58) Field of Classification Search
CPC .............. A61M 1/1656; A61M 1/1601; A61M 1/1607; A61M 1/1666; A61M 2205/502; A61M 2205/52
See application file for complete search history.

(56) References Cited

U.S. PATENT DOCUMENTS 9,526,822 B2 12/2016 Meyer et al.
9,724,455 B2 8/2017 Kopperschmidt et al.
(Continued)

FOREIGN PATENT DOCUMENTS

CN 103857419 B 6/2014
CN 104379189 A 2/2015
(Continued)

OTHER PUBLICATIONS

German Search Report for German Application No. 10 2016 107 589.2, dated Dec. 2, 2016, with translation—14 pages.
(Continued)

*Primary Examiner* — Anshu Bhatia

(57) ABSTRACT

A method and device for performing extracorporeal blood treatment utilizes a first concentrate connection configured to feed a first concentrate into the device as a basis for generating a dialysate, and a second concentrate connection configured to feed a second concentrate into the device as a basis for generating a dialysate. In operation, a first concentrate is fed into the device through the first concentrate connection. The method and device then switch over from feeding the first concentrate into the device through the first concentrate connection to feeding the second concentrate into the device through the second concentrate connection. The switchover step can be performed at a predetermined time during an ongoing blood treatment or after a predetermined period of time.

9 Claims, 2 Drawing Sheets

(52) U.S. Cl.
CPC ..... *A61M 1/1666* (2014.02); *A61M 2205/502* (2013.01); *A61M 2205/52* (2013.01)

(56) References Cited

U.S. PATENT DOCUMENTS

| | | |
|---|---|---|
| 10,076,735 B2 | 9/2018 | Jansson et al. |
| 2014/0018727 A1* | 1/2014 | Burbank ................ A61M 1/166 604/28 |
| 2014/0088442 A1* | 3/2014 | Soykan ................ A61B 5/6866 600/483 |
| 2015/0335808 A1 | 11/2015 | White et al. |
| 2016/0051949 A1* | 2/2016 | Jansson ................ G05D 11/138 366/162.1 |
| 2019/0262521 A1 | 8/2019 | Riemenschneider |

FOREIGN PATENT DOCUMENTS

| | | |
|---|---|---|
| CN | 105120913 A | 12/2015 |
| CN | 207950241 U | 10/2018 |
| DE | 19824057 C1 | 7/1999 |
| DE | 102013102914 A1 | 9/2014 |
| EP | 0160272 A2 | 11/1985 |
| EP | 0714668 A1 | 6/1996 |

OTHER PUBLICATIONS

European Search Report for European Application No. 17 167 785.9, dated Dec. 4, 2017, with translation—10 pages.
Chinese Office Action received in Application No. 201710277402.X dated Sep. 28, 2020, 16 pages.

* cited by examiner

DEVICE FOR EXTRACORPOREAL BLOOD TREATMENT INVOLVING A CHANGE OF CONCENTRATE

CROSS REFERENCE TO RELATED APPLICATIONS

This application is a continuation of, and claims priority under 35 U.S.C. § 120 to, U.S. application Ser. No. 15/495,449, filed Apr. 24, 2017, which claims priority under 35 U.S.C. § 119 to German application DE 10 2016 107 589.2, filed Apr. 25, 2016. The contents of U.S. application Ser. No. 15/495,449 and German application DE 10 2016 107 589.2 are incorporated by reference herein.

FIELD

The invention concerns a device for extracorporeal blood treatment involving a change of concentrate and refers in particular to a device for extracorporeal blood treatment in which during an ongoing treatment it is possible to change from a first concentrate to a second concentrate by self-controlled or automatic means.

BACKGROUND

A known device for extracorporeal blood treatment such as a dialysis unit or a dialysis machine comprises at least one treatment unit such as a dialyzer or a dialyzer facility, or a filter, ultrafilter or plasma filter, or another type of filter unit with a semi-permeable membrane which separates the treatment unit into two chambers. An extracorporeal blood circulatory system allows the blood taken from a patient to flow through the first chamber and back to the patient. At the same time, a dialysate (treatment fluid) flows in the opposite direction through a suitably designed circulatory system via the second chamber. The known device also comprises an infusion line for a substitution fluid, a fluid intake line connected to the second chamber on the intake side and a fluid outlet line connected on the outlet side to the second chamber.

In such devices for extracorporeal blood treatment, (liquid or dry) concentrates are used in canisters or containers as the basic substance for making the dialysate. These include acetate hemodialysis concentrates, acidic hemodialysis concentrates, bicarbonate concentrates, sodium hydrogen carbonate powder and the like, to mention just a few. They contain electrolytes such as sodium, chloride, potassium, calcium and magnesium. The dialysis device dilutes the concentrates with purified water to physiological levels before they can be used as dialysate and flow through the dialyzer.

Up until now, the correct selection of concentrates in adapting the dialysates to achieve optimum individualization of the therapy parameters and patient support has been a challenge to the user. In view of the increasing number of haemodiafiltration therapies in particular, it is becoming more and more common to change the concentrates by hand, which involves a brief interruption of the therapy. This ties up personnel and cannot always be carried out at precisely the stipulated time during the ongoing therapy. As a result of these limitations in terms of technology and personnel, a concentrate is frequently selected which does not provide optimum support for the therapy.

Known measures for adapting the course of treatment consist of changing the concentrate during an ongoing therapy at a time agreed on in advance with a doctor or selecting a concentrate which can be used for the entire duration of the therapy without a critical drop in the level of potassium occurring, for example, or, if complications occur during the course of therapy due to an excessively low potassium level, changing the concentrate manually in response to this. Systems are also known in which the concentrate is prepared from three components (so-called "three mix"), though these are technically very elaborate and costly, as well as being fraught with risk when it comes to monitoring. What is more, this type of application also limits other electrolytes since the levels of the latter are raised and/or lowered at the same time.

Up until now, the aforementioned known techniques have forced the user to draw on an application that is not ideally patient-oriented. The personnel required, the risks involved and the interruption of the therapy required to change the concentrate in the machine allow only an acceptable application rather than an optimum, patient-oriented therapy.

SUMMARY

One of the purposes of the invention is therefore to overcome the aforementioned problems and provide a device for extracorporeal blood treatment, which is geared towards improving the therapy outcome while at the same time making life easier for the user.

The invention also aims to ensure reliable application and at the same time make it possible to treat a patient in a more problem-free manner and with a better treatment result.

This object is achieved according to aspects of the invention by a device for extracorporeal blood treatment with the characteristics of the main claim. Advantageous embodiments of the invention are the subject of the dependent claims included.

The invention relates to the general notion of adapting the course of the patient's treatment by changing a concentrate during ongoing blood treatment or therapy, preferably automatically. For this purpose, a machine for extracorporeal blood treatment comprises a facility for supplying concentrate which is designed to change or switch over from a first concentrate to at least a second concentrate after a certain period of time. The concentrate can be provided in at least two canisters (containers, bags, cartridges). The doctor in charge notes down in a therapy protocol the type of concentrates and the time or times of the changeover. If during a therapy being conducted for the first time a specific change or switchover time is not yet known or has not yet been established, the therapy system can be set up to learn this automatically from one therapy to the next. In other words, a changeover time can be recorded as a specification for the subsequent therapy. The hardware can be designed to use an existing bicarbonate connection as a second acid inlet if necessary. The automatic switchover and checking of the concentrates can be carried out on a software-supported basis.

This enables the doctor to respond separately to the major shift in electrolyte levels, especially at the beginning of the therapy. Since the blood count levels can quickly change, the doctor can more effectively prepare and quickly adapt therapy progress of the treatment with the choice of second concentrate and the time of application with an adjusted diffusion pressure.

The invention thus provides a technical solution which gives the user automatic and reliable support. It is not necessary to make do with an interruption of therapy as caused by having to change concentrates. Nor is any delay caused in the time at which the therapy ends.

Specifically, the object is achieved by a device for extracorporeal blood treatment, comprising: at least a first concentrate connection which is set up to feed at least a first concentrate into the device for extracorporeal blood treatment as the basis for generating a dialysate; at least a second concentrate connection which is set up to feed at least a second concentrate into the device for extracorporeal blood treatment as the basis for generating a dialysate; whereby the device for extracorporeal blood treatment is configured to switch over from supplying the at least first concentrate to supplying the at least second concentrate at a predefined time or after a predefined period of time during an ongoing blood treatment.

The device is preferably set up to carry out the changeover from supplying the at least first concentrate to supplying the at least second concentrate automatically.

The first concentrate may be a first acid concentrate and the first concentrate connection may be a first acid concentrate connection, and the second concentrate may be a second acid concentrate and the second concentrate connection may be a second concentrate connection.

The first concentrate and/or the second concentrate may be provided in the form of a liquid concentrate supply or dry concentrate supply in a first and a second concentrate container respectively, wherein the first concentrate container is capable of being connected to the first concentrate connection in a way which is permeable to concentrate and the second concentrate container is capable of being connected to the second concentrate connection in a way which is permeable to concentrate.

The at least one existing bicarbonate connection may be configured as the first or the second concentrate connection in such a way that the first or the second concentrate can be supplied to the device via the existing bicarbonate connection, wherein in this case bicarbonate can be supplied separately from the existing bicarbonate connection.

At least another concentrate connection may be provided in addition to the existing concentrate connections as the first or the second concentrate connection.

A large number of types of usable first and second concentrates may be stored in advance in a storage facility of the device and the device preferably allows at least the first concentrate and at least the second concentrate to be selected from the known large number of usable concentrates.

The device may be configured to protocol a concentrate changeover time in the course of an ongoing treatment and to save this and make it available as a predefined time for at least one subsequent treatment.

The device may be configured to learn and save at least one correct patient-oriented selection of concentrates, mixture ratios of the same and a connection assignment to selected concentrates over the course of several treatments.

Where a change in the concentrate-related mixing ratio is registered by the device, the device may be configured to request that a user verify and/or confirm a correct connection of at least one of the concentrate containers being used.

BRIEF DESCRIPTION OF THE DRAWINGS

The invention is best understood from the following detailed description when read in connection with the accompanying drawings. Included in the drawings are the following figures.

DETAILED DESCRIPTION

Figure 1:
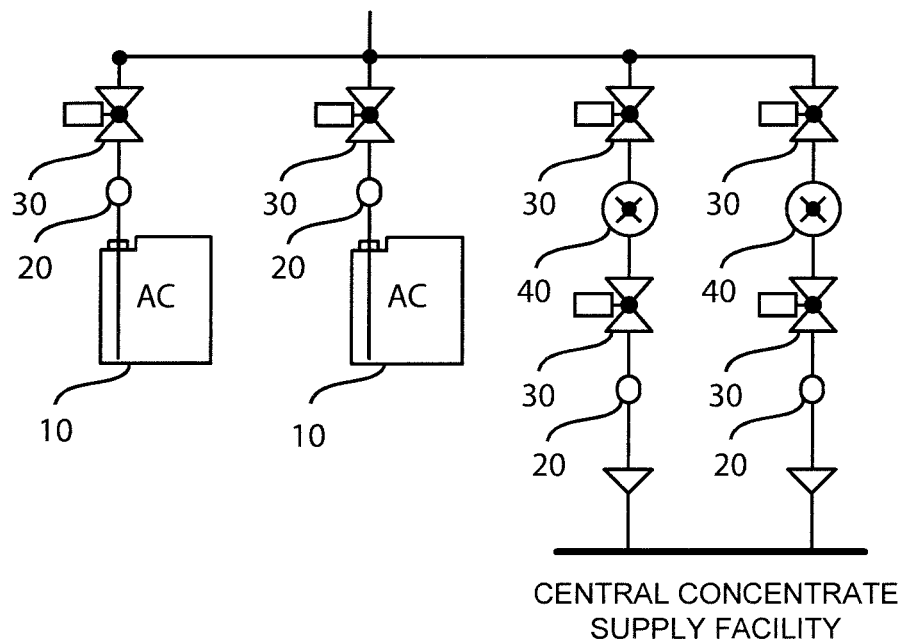
FIG. 1 shows, schematically simplified and in sections, a basic set-up of a concentrate supply facility in a device for extracorporeal blood treatment.

In the following detailed description, elements and/or components which are identical or perform an identical function may be labelled identically and/or with the same reference numerals in the individual figures and not be described redundantly, for the purpose of expediency. In cases in which an embodiment is functionally the same as at least one previous embodiment, i.e. it comprises the same functions, set-ups and/or process or operating sequences, only the differences are addressed for the purpose of expediency.

A device for extracorporeal blood treatment such as a dialysis machine for the purification of the blood of a patient, where the latter's kidney function is limited or has failed, comprises a dialyzer which is passed through firstly by the patient's blood to be purified and secondly by the dialysate or dialysis solution, preferably according to the counterflow principle, wherein certain solutes (e.g. urea) pass from the blood to the dialysate.

The system, structure, components and functioning of the aforementioned device for extracorporeal blood treatment, which can in particular be a dialysis device or a dialysis machine, are fundamentally known and are therefore included in the following and not described in any further detail.

Such a device preferably also comprises a predefined number of connections with which an acid concentrate and/or a bicarbonate concentrate can be fed in to create the dialysate required. Generally speaking, individual connections allow containers 10 of a predetermined type such as PE canisters to be connected to larger supplies of concentrate or flexible plastic bags or cartridges with hose pipes. Liquid concentrate can, for example, be conveyed via at least one intake lance from a container 10 (canister, bag) of a suitable nature and size and fed to the device. Dry concentrate stored in bag-type or cartridge-type containers can, for example, be dissolved immediately prior to use directly at the device. What is more, the supply of concentrate to the device can be integrated in an essentially known concentrate supply facility forming part of the device.

FIG. 1 shows, schematically simplified and in sections, a basic set-up of a concentrate supply facility in a device for extracorporeal blood treatment as can be configured in the following embodiments.

According to FIG. 1, at least two acid concentrate connections can be provided on the device for extracorporeal blood treatment for connecting at least two acid concentrate supply vessels or containers 10. An intake lance can be immersed in each acid concentrate supply in the containers 10, with which a predetermined amount of concentrate can be conveyed from the supply and fed to the device for extracorporeal blood treatment or to a central concentrate supply facility forming part of the same. Concentrate filters 20, valves 30, pumps 40 and the like can be arranged in the relevant fluid lines which can be suitably designed and controllable to carry the required amounts of concentrate. A dry concentrate supply facility can also be mounted in a comparable manner with type-specific differences, for example in terms of a section for dissolving the dry concentrate at the device.

Figure 2:
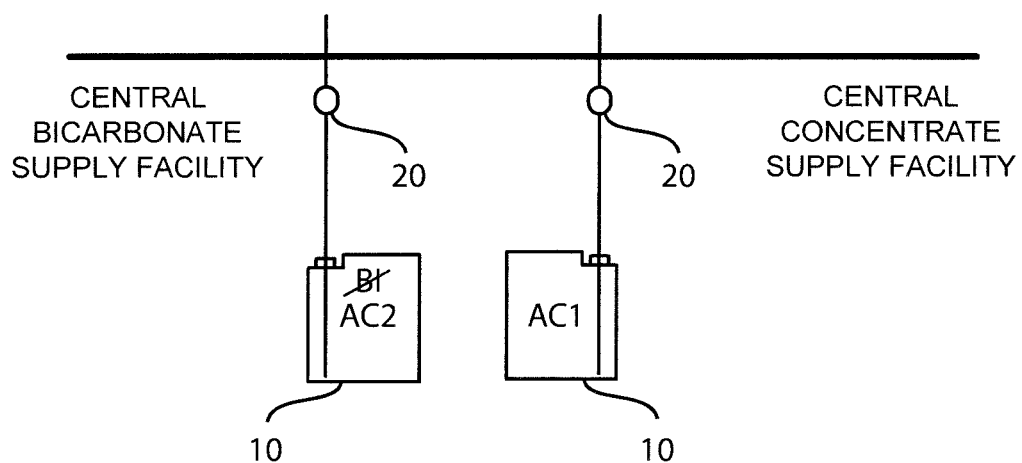
FIG. 2 shows, schematically simplified and in sections, a set-up of a concentrate supply facility in a device for extracorporeal blood treatment according to a first embodiment of the device for extracorporeal blood treatment configured for an automatic change of concentrate.

FIG. 2 shows, schematically simplified and in sections, a set-up of a concentrate supply facility in a device for extracorporeal blood treatment according to a first embodiment of the device for extracorporeal blood treatment configured for a change of concentrate.

An existing device for extracorporeal blood treatment can, for example, comprise a connection for a bicarbonate concentrate (BI), at which bicarbonate or bicarbonate concentrate can be fed from the supply or container with a central bicarbonate supply facility forming part of the device, and a connection for a first acid concentrate (AC1), at which the first acid concentrate can be fed from the supply or container 10 with a central bicarbonate supply facility forming part of the device.

According to aspects of the invention, at least two acid concentrate connections are incorporated so as to be able to provide a first (AC1) and a second (AC2) acid concentrate at the device, between which it is possible to initiate a change during the ongoing therapy or blood treatment.

An automated central concentrate supply facility can, for example, be configured with at least three connections, each with an intake lance or intake rod inlet. In this case, no change to the hardware configuration is required, and it is possible to provide a first concentrate at a first inlet and a second concentrate at a second inlet, wherein bicarbonate concentrate can additionally be provided at a third inlet.

According to the first embodiment shown in FIG. 2, a device originally with two intake rod inlets has a connection for the device's bicarbonate supply facility which is used and configured as a connection for a second acid concentrate (→AC2), and, since the intake rod inlet originally intended for bicarbonate is not required, the device is configured or extended in its design to supply bicarbonate from containers provided from other sources such as bags or cartridges (not shown here).

Figure 3:
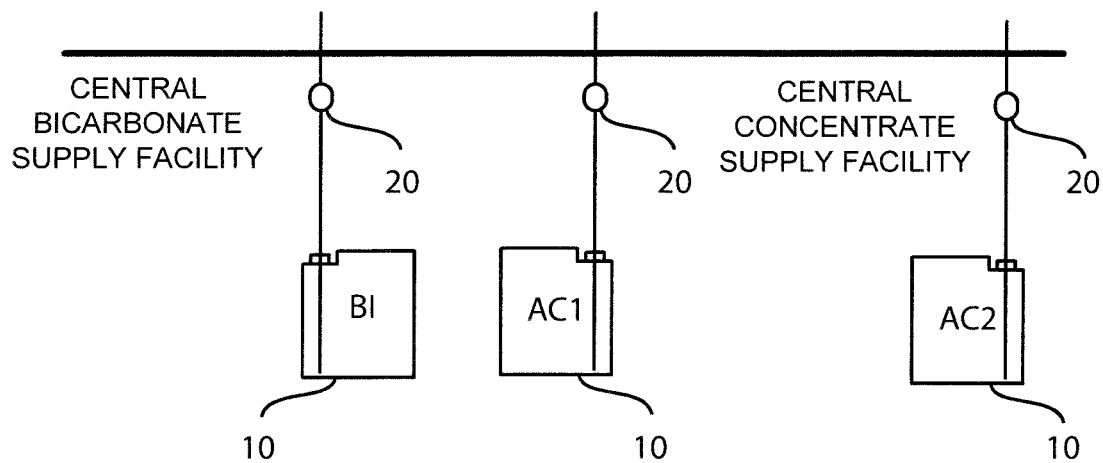
FIG. 3 shows, schematically simplified and in sections, a set-up of a concentrate supply facility in a device for extracorporeal blood treatment according to a second embodiment of the device for extracorporeal blood treatment configured for an automatic change of concentrate.

FIG. 3 shows, schematically simplified and in sections, a set-up of a concentrate supply facility in a device for extracorporeal blood treatment according to a second embodiment of the device for extracorporeal blood treatment configured for an automatic change of concentrate.

According to the embodiment shown in FIG. 3, a device originally with two intake rod inlets, shown on the left-hand side in FIG. 3, has been extended by at least one additional connection for at least a second acid concentrate (AC2), shown on the right-hand side in FIG. 3. The device's original bicarbonate supply facility (BI) and acid concentrate supply facility with a first acid concentrate (AC1) are preserved. As such, a total of three connections and/or intake rods are provided, wherein in this second embodiment only the at least two acid connections AC1, AC2 are able to switch over or change automatically.

In addition to this, an extended configuration of the control and/or activation can be provided to support the user such that the device allows at least a first and a second concentrate or a first and second amount of concentrate can be predetermined and entered, and, in accordance with a time specification or setting, a self-controlled or automatic change can be carried out by the device from the first concentrate to the second concentrate.

In the relevant therapy context, a patient card and/or network parameter entry can also be provided such that a therapy system displays at least one therapy progress changeover time and/or concentrate selection at any time.

A fundamental way of functioning and operation of the above set-up can be configured as follows in connection with the device for extracorporeal blood treatment.

After an initializing entry procedure, carried out by technical personnel for example, all the used or usable concentrates are stored or saved in the device for extracorporeal blood treatment and are therefore known to the device.

During preparatory measures and/or a self-test, a check for correctness is carried out via mixture ratios, for example to check the correct type and/or proper connection and the patient-oriented nature of the concentrate and/or concentrate connection. Prior to the start of therapy, the user confirms that the selection of concentrates and the assignment of concentrates to the connections are correct.

A concentrate changeover time logged during a prior therapy can be taken as a read-out and used as a specified value for a next or subsequent therapy, i.e. such a changeover time is available in the device as a specification for the next therapy.

Once the therapy has started, the system or the device can be set up to automatically learn patient-oriented concentrates and their (mixing or dilution) ratios in each case and to save them in a storage facility provided.

Furthermore, the system or the device can, when recording a change in mixing ratio, be configured to ask the user about this and to call upon the user to confirm, for example after an additional visual check, the right or correct connection of the concentrate container, based on the mixing ratio calculated by the device. Here, a right or correct connection of the concentrate container can refer in particular to an error-free and proper connection to the device or an interconnection with the device.

It goes without saying that the invention is not limited to the embodiments described and their modifications but that, within the scope of protection defined by the claims below, combinations of at least parts of these embodiments, modifications and equivalents can arise which are nonetheless obvious to the person skilled in the art.

What is claimed:

1. A method of extracorporeal blood treatment using a device having a first concentrate connection configured to feed a first concentrate into the device as a basis for generating a dialysate, and a second concentrate connection configured to feed a second concentrate into the device as a basis for generating a dialysate, the method comprising the steps of:
    A) feeding the first concentrate into the device through the first concentrate connection;
    B) stopping said feeding of the first concentrate into the device through the first concentrate connection;
    C) starting a feeding of the second concentrate into the device through the second concentrate connection after stopping said feeding of the first concentrate into the device through the first concentrate connection;
    D) registering a change in a concentrate-related mixing ratio; and
    E) requesting at least one of a verification or confirmation of a correct connection of at least one concentrate container being used,
    wherein step C) is performed at a predetermined time during an ongoing blood treatment or after a predetermined period of time.

2. The method of extracorporeal blood treatment according to claim 1, wherein step C) is carried out automatically.

3. The method of extracorporeal blood treatment according to claim 1, wherein the first concentrate is an acid concentrate and the first concentrate connection is a first acid concentrate connection, and the second concentrate is an acid concentrate and the second concentrate connection is a second acid concentrate connection.

4. The method of extracorporeal blood treatment according to claim 1, wherein at least one of the first concentrate and the second concentrate is provided in the form of a liquid concentrate supply or a dry concentrate supply in at least one of a first or a second concentrate container, respectively, wherein the first concentrate container is connected to the first concentrate connection in a way which is permeable to concentrate and the second concentrate container is connected to the second concentrate connection in a way which is permeable to concentrate.

5. The method of extracorporeal blood treatment according to claim 1, wherein at least one existing bicarbonate connection is configured as the first or the second concentrate connection in such a way that the first or the second concentrate can be supplied to the device via the at least one existing bicarbonate connection, wherein bicarbonate is supplied separately from the at least one existing bicarbonate connection.

6. The method of extracorporeal blood treatment according to claim 1, wherein the device comprises at least one further concentrate connection.

7. The method of extracorporeal blood treatment according to claim 1, wherein a large number of types of usable first and second concentrates are stored in advance in a storage facility of the device, and the first concentrate and the second concentrate are selected at the device from the large number of usable concentrates known to the device.

8. The method of extracorporeal blood treatment according to claim 1, further comprising the steps of:
    logging a concentrate changeover time in the course of an ongoing treatment; and
    making said concentrate changeover time available as a predefined time for at least one subsequent treatment.

9. The method of extracorporeal blood treatment according to claim 1, further comprising the steps of learning and saving at least one correct patient-oriented selection of concentrates, mixture ratios of the same and a connection assignment to selected concentrates over the course of several treatments.

* * * * *